(12) United States Patent
Furey (10) Patent No.: US 9,844,452 B2
(45) Date of Patent: *Dec. 19, 2017

(54) IMPLANTABLE FLOW ADJUSTER

(71) Applicant: Cook Medical Technologies LLC, Bloomington, IN (US)

(72) Inventor: Aidan Furey, Copenhagen (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 67 days.

This patent is subject to a terminal disclaimer.

(21) Appl. No.: 14/456,160

(22) Filed: Aug. 11, 2014

(65) Prior Publication Data
US 2015/0051694 A1 Feb. 19, 2015

(30) Foreign Application Priority Data
Aug. 13, 2013 (GB) ................................ 1314488.6

(51) Int. Cl.
*A61F 2/82* (2013.01)
*A61F 2/06* (2013.01)
*A61F 2/91* (2013.01)

(52) U.S. Cl.
CPC ..................... *A61F 2/82* (2013.01); *A61F 2/91* (2013.01); *A61F 2002/068* (2013.01); *A61F 2002/823* (2013.01)

(58) Field of Classification Search
CPC ................. A61F 2/24; A61F 2/2478
USPC ......................... 623/1.24, 2.1–2.19
See application file for complete search history.

(56) References Cited

U.S. PATENT DOCUMENTS

| 5,197,980 A | * | 3/1993 | Gorshkov | A61F 2/2403 137/512.1 |
| 8,142,387 B2 | | 3/2012 | Heise et al. | |
| 2002/0179166 A1 | | 12/2002 | Houston et al. | |
| 2002/0198591 A1 | | 12/2002 | Stergiopulos | |
| 2003/0100945 A1 | | 5/2003 | Yodfat et al. | |
| 2007/0276467 A1 | * | 11/2007 | Kalmann | A61F 2/2418 623/1.24 |
| 2007/0288086 A1 | * | 12/2007 | Kalmann | A61F 2/2418 623/1.24 |
| 2008/0140110 A1 | | 6/2008 | Spence | |

(Continued)

FOREIGN PATENT DOCUMENTS

| EP | 0804908 A1 | 11/1997 |
| GB | 2382776 A | 6/2003 |

(Continued)

*Primary Examiner* — Thomas J Sweet
(74) *Attorney, Agent, or Firm* — Brinks Gilson & Lione (57) ABSTRACT

An implantable flow adjuster (20) includes proximal and distal support rings (22, 24) which support a flow adjuster panel (26). The flow adjuster panel (26) divides the lumen through the device (20) into two sections, one of reducing cross sectional area and the other of increasing of increasing cross sectional area. The two sections (40, 42) cause, respectively, an increase in blood pressure and blood flow and a decrease in blood pressure and blood flow. These result is a pressure differential beyond the distal end of the device (20). This pressure differential can be used to divert blood flow away from the neck (14) into an aneurysm (12), thus to reduce pressure and wall sheer stress within the aneurysm in order to assist in the repair of the vessel.

20 Claims, 6 Drawing Sheets

(56) References Cited

U.S. PATENT DOCUMENTS

| | | | |
|---|---|---|---|
| 2009/0254176 A1* | 10/2009 | Butera | A61F 2/2418 623/1.24 |
| 2010/0106180 A1 | 4/2010 | Strother et al. | |
| 2010/0256731 A1 | 10/2010 | Mangiardi | |
| 2011/0066224 A1* | 3/2011 | White | A61F 2/2412 623/1.15 |
| 2011/0230956 A1* | 9/2011 | White | A61F 2/2412 623/1.16 |
| 2012/0130476 A1* | 5/2012 | Paul | A61F 2/2412 623/1.13 |
| 2012/0136429 A1* | 5/2012 | Hinchliffe | A61F 2/2418 623/1.18 |
| 2013/0123908 A1* | 5/2013 | Hinchliffe | A61F 2/2475 623/1.24 |
| 2014/0343664 A1* | 11/2014 | Furey | A61F 2/06 623/1.18 |

FOREIGN PATENT DOCUMENTS

| | | |
|---|---|---|
| GB | 2423476 A | 8/2006 |
| WO | WO 2011/004179 A1 | 1/2011 |
| WO | WO2012/102919 | 8/2012 |

* cited by examiner

Fig. 18

IMPLANTABLE FLOW ADJUSTER

This application claims the benefit of the filing date of United Kingdom (GB) patent application number 1314488.6, filed Aug. 13, 2013.

TECHNICAL FIELD

The present invention relates to an implantable medical device, in particular for altering the characteristics of blood flow within the vessel of a patient.

BACKGROUND ART

Many factors contribute to the formation of saccular aneurysms, particularly neural aneurysms. One of the major contributors is wall shear stress (WSS), which in addition to hypertension leads to a reduction in the elastic tissue of the tunica media, thereby contributing to the formation of the aneurysm. The effect of wall shear stress is heightened at certain anatomical geometries such as bifurcations.

It is known to try to treat aneurysms by filling the aneurysmal sac with filler such as a prosthetic coil. The methodology behind the use of prosthetic coils is to establish a hard thrombus formation within the sac of the aneurysm as a means of isolating the aneurysm wall from the flow of blood. While this can be effective in the treatment of many types of aneurysm, it is less effective when the aneurysm occurs at a bifurcation or trifurcation, such as at the base of the basilar artery. Furthermore, filling an aneurysm does not necessarily reduce the pressure applied to the wall of the aneurysm sac caused by the blood flow.

It is also known to close off the entrance to the aneurysmal sac or to divert the flow of fluid therefrom, but known devices do not always effectively reduce blood flow into the sac or pressure applied to its wall.

Examples of devices for treating aneurysms can be found in U.S. 2002/179166, U.S. 2002/0198591, U.S.-2003/0100945, U.S.-2010/0106180 and WO 2012/102919.

SUMMARY OF THE INVENTION

The present invention seeks to provide improved treatment of aneurysms, in particular an implantable flow adjuster and method of diverting flow from an aneurysm.

According to an aspect of the present invention, there is provided an endoluminal flow adjuster having a diameter, a length delimited by proximal and distal ends, and providing a passage for the flow of fluid therethrough; the flow adjuster including at least one support structure providing proximal and distal supports spaced in a longitudinal direction of the flow adjuster between the proximal and distal ends; and an adjuster element including a panel having a length extending in the longitudinal direction, said panel being disposed between and supported by the proximal and distal supports, the panel dividing the passage through the flow adjuster into first and second parts varying in size over at least a part of the length of the flow adjuster.

Advantageously, the first and second parts provide unequal flow cross sectional areas through the flow adjuster, thereby to create a fluid pressure differential between the first and second parts.

The division of the passage of fluid flow through the lumen of the flow adjuster into uneven paths creates pressure differentials in the vessel, in practice a zone of higher pressure and a zone of lower pressure. This pressure differential can alter the flow path of fluid and in practice to pass across the neck of an aneurysm rather than into the aneurysm. As a result, there is a reduction of blood pressure in the aneurysm and thereby of wall shear stress, which can help in the process of remodelling of the aneurysm and reformation of healthy vessel wall.

Thus, in the preferred embodiment, the first and second parts create two flows of fluid through the flow adjuster, one having a higher fluid pressure relative to the other.

Advantageously, the panel is formed of a sheet of material, which may be substantially impermeable. In some embodiments, the panel has perforations or slots therein, the panel providing a barrier to blood therethrough; that is the slots or perforations are of a size that they do not significantly alter the behaviour of blood passing through the flow adjuster.

The panel is preferably of substantially uniform thickness.

In practice, the panel provides a flow constriction through the flow diverter in one of said first and second parts, the flow constriction varying in transverse cross-sectional area along the length of the panel.

In an embodiment, the panel is transversally curved to provide said first and second flow parts of unequal size. Advantageously, the transverse curvature of the panel varies along the length of the panel.

In another embodiment, the panel extends from a position close to one side of the flow adjuster at the proximal support to a position close to an opposing side of the flow adjuster at the distal support.

In this embodiment, the panel could be a substantially flat structure or could have the curvature mentioned above.

In another embodiment, the panel has a concave or convex shape between the ends thereof. The ends of such a panel may be substantially straight.

Preferably, the proximal and distal supports are ring-shaped. They are advantageously radially compressible. In an embodiment, the proximal and distal supports are stents.

The proximal and distal supports may be made of an elastically deformable material, such as a spring material or a shape memory material.

The proximal and distal supports may be separate from one another, but in other embodiments they are coupled to one another, such as by a wire, tether or tie bar, while in other embodiments they could be part of a single stent structure.

There is also disclosed a method of altering the characteristics of blood flow within the vessel of a patient including the steps of:

deploying in a vessel an endoluminal flow adjuster having a diameter, a length delimited by proximal and distal ends, and providing a passage for the flow of fluid therethrough; the flow adjuster including at least one support structure providing proximal and distal supports spaced in a longitudinal direction of the flow adjuster between the proximal and distal ends; and an adjuster element including a panel having a length extending in the longitudinal direction, said panel being disposed between and supported by the proximal and distal supports, the panel dividing the passage through the flow adjuster into first and second parts varying in size over at least a part of the length of the flow adjuster;

wherein the adjuster element causes blood flow in the vessel to be split into first and second parts having different flow velocities, the flow adjuster being deployed in an orientation in the vessel to create a pressure differential across the vessel at a treatment point of the vessel.

In the preferred embodiment, the method reduces the flow of fluid into an aneurysm sac. In practice, this is achieved by orienting the flow adjuster to create a pressure differential across the width of the vessel at the entrance to the sac, which pressure differential causes blood to flow across the neck of the aneurysm rather than into it. This may, for instance be by ensuring that the pressure differential causes the flow to adjust laterally across the vessel away from the neck of the aneurysm.

Other features are disclosed in the description of the preferred embodiments of the invention which follows. It is to be understood that all such features are applicable to all embodiments disclosed herein.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Described below are various embodiments of flow adjuster for altering the flow of blood within a patient's vessel. The term flow adjuster as used herein encompasses the guiding of the flow of blood within a vessel, in particular to alter the pressure profile across the diameter of the vessel and in the preferred embodiments to create a pressure differential across the width of the vessel at the point of treatment in the vessel, in this example, at the neck of an aneurysm.

The preferred embodiments are described in connection with a flow adjuster intended for implantation in the cerebral vessels. It is to be understood, however, that the teachings herein can be applied in the alteration of the flow in any vessel of a patient. It will be appreciated that the dimensions of the device will differ for different vessel sizes.

Figure 1:
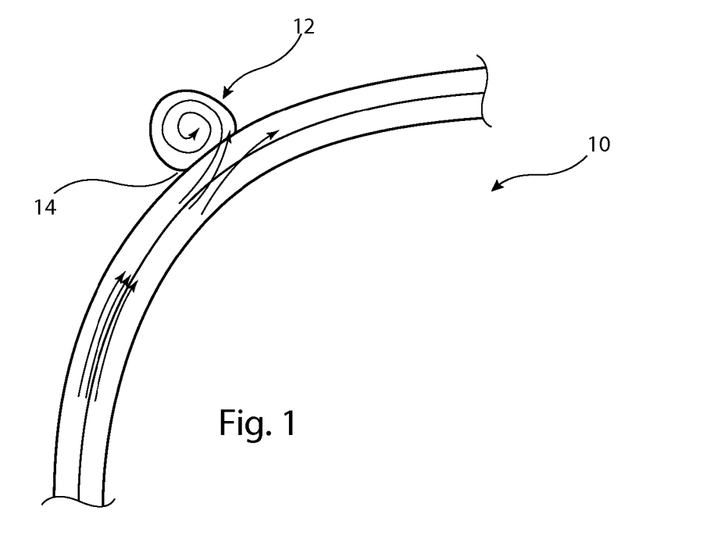
FIG. 1 is a schematic view of a vessel having an aneurysm.

Referring to FIG. 1, there is shown an example of a vessel 10 which has developed an aneurysm 12, in this example in a part of the vessel wall on the outside of the curve in the vessel 10. The aneurysm sac 12 has a neck 14, which often has a diameter smaller than the maximum diameter of the aneurysm sac. Although many factors can contribute to the formation of a saccular neuro aneurysm, the development of an aneurysm in such a location is often triggered as a result of higher blood pressure at that point of the vessel and thus of increased wall shear stress (WSS), in particular in cases where the vessel wall has weakened or the patient is also suffering from hypertension. These factors lead to a reduction in the elastic tissue of the tunica media, thereby contributing to the formation of the aneurysm. Blood will continue to flow into the aneurysm sac 12, thereby contributing to a maintenance of wall shear stress in the aneurysm and growth of the sac 12 with further consequential weakening of the tunica media. Eventually the vessel wall can rupture causing hemorrhaging.

The devices taught herein are designed to reduce or stop of the flow of blood into the aneurysm by altering the blood pressure at the neck 14 of the aneurysm and consequently reducing the flow of blood into the aneurysm sac 12 itself.

The embodiments of flow adjuster disclosed herein create a pressure differential across the diameter of the vessel 10, preferably just upstream of the neck 14, so as to divert the flow of blood away from the aneurysm. This is achieved by splitting the blood flow in the vessel 10 into at least two portions and subjecting these to different cross-sectional passages, typically one narrowing and the other widening, which generates the desired pressure differential. Beyond the flow adjuster, that is downstream thereof, the pressure of the blood can equalize again, in so doing causing an alteration of the flow of blood across the vessel and in practice away from the aneurysm.

Figure 2:
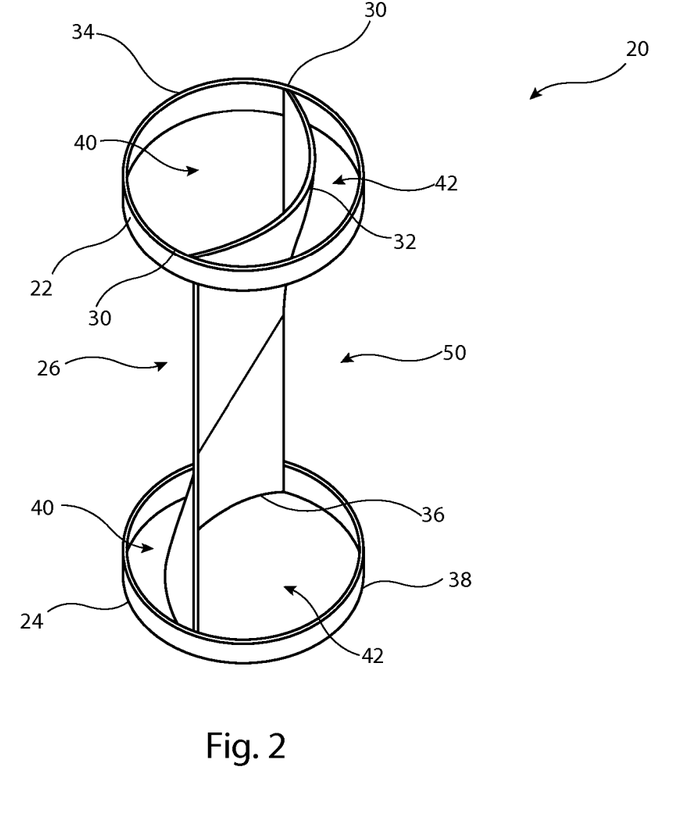
FIG. 2 perspective view of an embodiment of flow adjuster.
Figure 3:
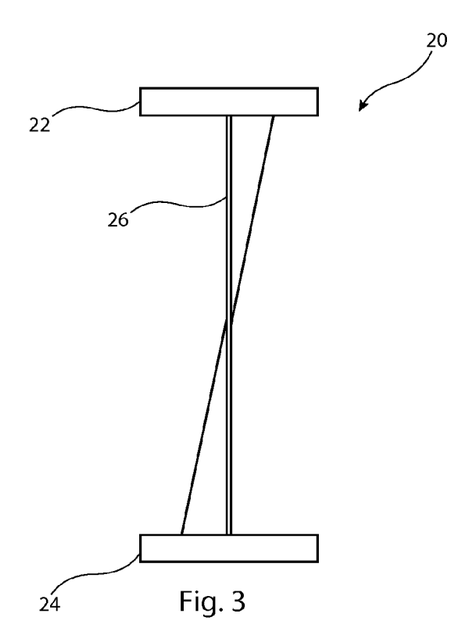
FIGS. 3 and 4 are side and front elevational views of the flow adjuster of FIG. 2.
Figure 4:
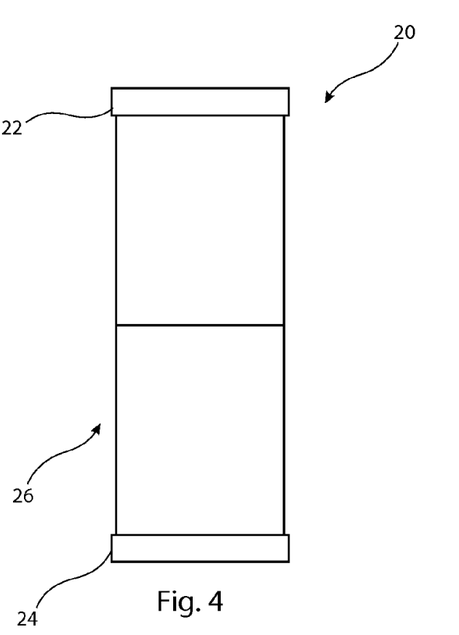
Figure 5:
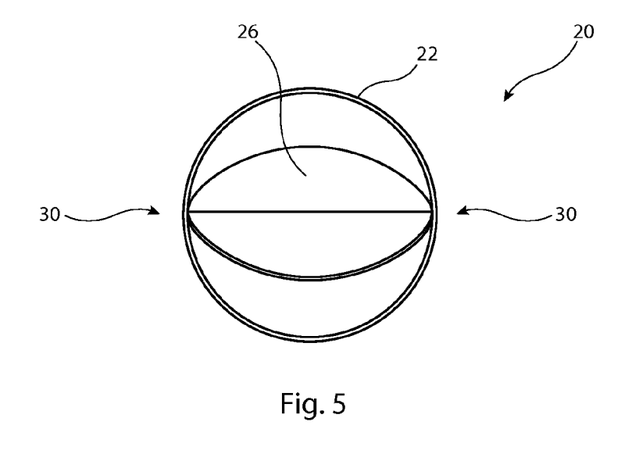
FIG. 5 is a plan view of the flow adjuster of FIGS. 2 to 4.

A first embodiment of flow adjuster 20 is shown in FIGS. 2 to 5, FIG. 2 being a perspective view, FIGS. 3 and 4 being side and front elevational views respectively and FIG. 5 being a plan view. The embodiment of flow adjuster 20 shown in these Figures, as well as the other embodiments described below, are sized to fit within a cerebral vessel of a patient, and may have a length of around 10 to 15 mm and a diameter of around 2 to 5 mm. The structure taught herein, though, can be sized for a wide variety of vessels including much larger arteries.

The flow adjuster 20 includes a proximal support 22 which in this embodiment is in the form of a resilient ring of generally circular form. The distal support 22 is located at the distal extremity of the flow adjuster 20. A distal support 24, again being in this embodiment in the form of an annular ring of resilient material, is located at the proximal end of the flow adjuster 20. It is preferred that the proximal and distal supports 22, 24, form the proximal and distal extremities, respectively, of the flow adjuster 20.

Supported by and extending between the proximal and distal supports 22, 24 is an adjuster element 26 which in this example is a substantially rectangular panel made of impermeable or substantially impermeable material and is transversally curved in the longitudinal direction of the flow adjuster 20. More specifically, the panel 26 is in this embodiment attached at diametrically opposite sides 30 of each support 22, 24. The attachment may be by a solder joint, welding, use of bonding agent or any other suitable attachment method. In this embodiment, the panel 26 is attached to the supports 22, 24, such that the proximal edge 32 of the panel 26 is aligned with the proximal edge 34 of the proximal support 22, while the distal edge 36 of the panel 26 is aligned with the distal edge 38 of the distal support 24. In other embodiments, the edges 32, 36 of the panel 26 may be attached at any location within the length, or depth, of the support rings 22, 24.

The proximal and distal supports may be made of a spring material such as spring steel, but are preferably made of a shape memory material, preferably a shape memory alloy such as nickel titanium alloy (Nitinol). In another example they could be made of cobalt chromium. The panel 26 may be made of the same material as the proximal and distal supports 22, 24 but may be made of other materials. These materials and other materials preferably used for the device 20 are anti-thrombotic material.

In the preferred embodiments the device is made of radiopaque materials or includes radiopaque markers. In the preferred embodiment, radiopaque markers or material are provided in the support rings 22, 24.

It will be appreciated that when made of a spring or shape memory material, the device 20 will exhibit resilience, for example compressibility in the radial direction, yet will exert a force tending it to its rest shape, that is its shape when not subjected to an external force. The device can thus be radially compressed in an introducer assembly for delivery and will expand when released from the introducer assembly constraints, in practice until it abuts and presses against the vessel walls as described in detail below. When made of a shape memory material, the device can be manufactured to have a transition temperature around body temperature and thus to exhibit its elastic return force only once deployed in the patient.

The proximal and distal support rings 22, 24 may be continuous rings of strip material or wire. In other embodiments they may have other configurations, such as a split ring, or a conventional stent ring having, for example, a sinusoidal or zigzag shape for radial compressibility. Furthermore, each of the proximal and distal support rings 22, 24 may be made of a single element but could in other embodiments be a set of annular elements, such as turns of a coil, of a strip or the like.

For a device 20 for cerebral applications, the wall thickness of the support elements 22, 24 and of the adjuster element 26 is preferably between about 0.5 mm to about 2.0 mm.

The panel 26 has a curvature which in this embodiment varies along the length of the panel, that is from the distal to the proximal ends of the device. As can be seen in particular in FIG. 2, the panel 26 has at the proximal end 22 a curvature which could be said to be concave when viewed from the left and consequentially convex when viewed from the right in the drawing. This curvature divides the annular space within the proximal support 22 into first and second sections 40 and 42 of unequal cross-sectional area.

As will be apparent from FIG. 2 in particular, the curvature of the panel 26 varies along the length of the panel from the proximal end 22 to the distal end 24, and in particular reverses at the distal end 24 such that its curvature is opposite that at the proximal end 22. Specifically, the curvature of the panel 26 lessens from the proximal end 22 towards the centre point 50 of the device 20 and then increases again, in the opposite direction, until the distal end 24.

Considering the device 20 in situ in a patient's vessel, the supports 22 and 24 will abut and press against the vessel walls and as a result the vessel wall will provide a tubular lumen through the centre of the device 20. The panel 26 divides that lumen into first and second parts or sections 40, 42, of varying cross-sectional area. If one considers the sections 40 and 42 from the proximal end 22 to the distal end 24, the section 40 has a larger transverse cross-sectional area at the proximal end 22, caused by the concavity of the panel 26 at this point, which then reduces in size towards the distal end 24, where the panel 26 is convex at that side of the device 26. On the other hand, the section or part 42 has a small transverse cross-sectional area at the proximal end 22 which then increases towards the distal end 24. Fluid flowing from the proximal end 22 to the distal end 24 will therefore split with more entering the section 40 than the section 42 due to their size differences. However, as the section 40 reduces in cross-sectional area along the length of the device 26, the flow speed and pressure of the fluid in this side will increase through the length of the device 20. By contrast, a lesser proportion of fluid will enter the device 20 through the section or part 42 but this will reduce in pressure and speed towards the distal end 24 as a result of the increasing cross-sectional area of the part or section 42.

As a result, fluid exiting the device 20 at the distal end 24 will have a relatively high pressure and low flow rate at the exit of section 40, and a relatively low pressure and low flow rate at the exit of section 42. This results in a pressure differential of fluid exiting the device 20 at the distal end 24, in a direction orthogonal to the tangent to the panel 26, in other words orthogonal to the line through the ends 30. This pressure differential causes an alteration in the flow of fluid beyond the device 20, from the high pressure side to the low pressure side. The effect of this in a vessel is shown and described with reference to FIGS. 17 and 18.

With reference to FIGS. 2 to 5, it will be appreciated that the flow adjuster 20 is sized such that the proximal and distal supports 22, 24 fit within a patient's vessel so as to press against the internal vessel walls to keep the flow diverter in position. The side edges of the panel 26 are preferably shaped and sized so as to extend to the lateral periphery of the flow adjuster 20 and in particular to the vessel walls. In this regard, the thickness of the preferred support elements 22, 24 will generally be immaterial with respect to the contact of the side edges of the panel 26 with the vessel walls given the pliancy of the vessel walls.

It will be appreciated that the panel 26 of the embodiment of FIGS. 2 to 5 will not be rectangular when laid flat given its varying curvature but will have a waisted shape consistent with the changes in its curvature.

Figure 6:
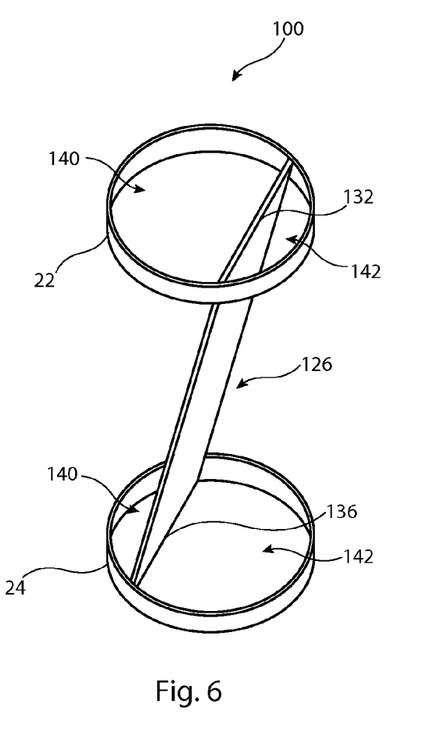
FIG. 6 is a perspective view of another embodiment of flow adjuster.
Figure 7:
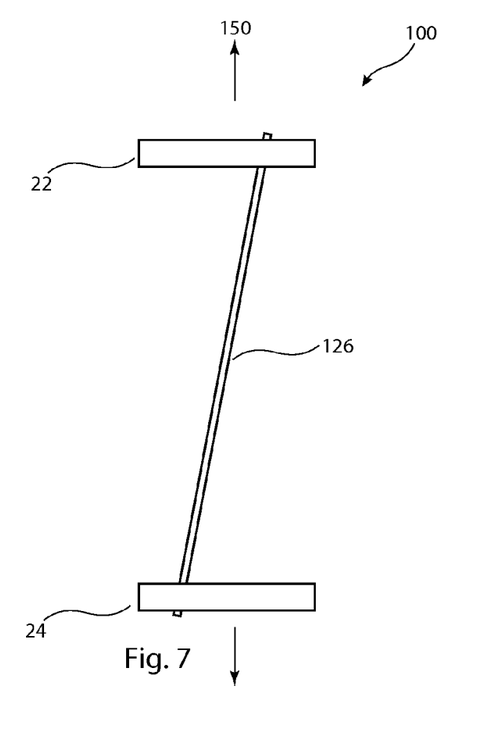
FIGS. 7 and 8 are side and front elevational views of the flow adjuster of FIG. 6.
Figure 8:
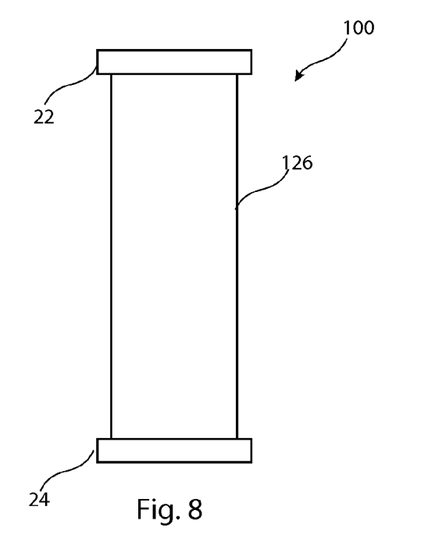
Figure 9:
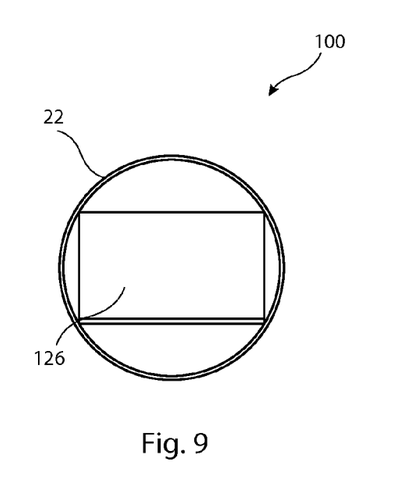
FIG. 9 is a plan view of the flow adjuster of FIGS. 6 to 8.
Figure 10:
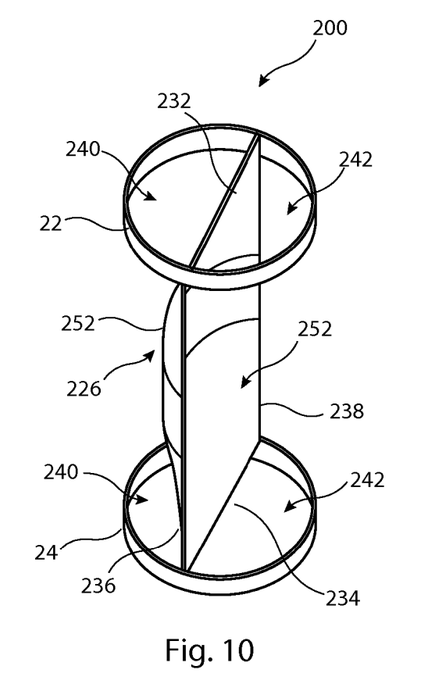
FIG. 10 is a perspective view of another embodiment of flow adjuster.
Figure 11:
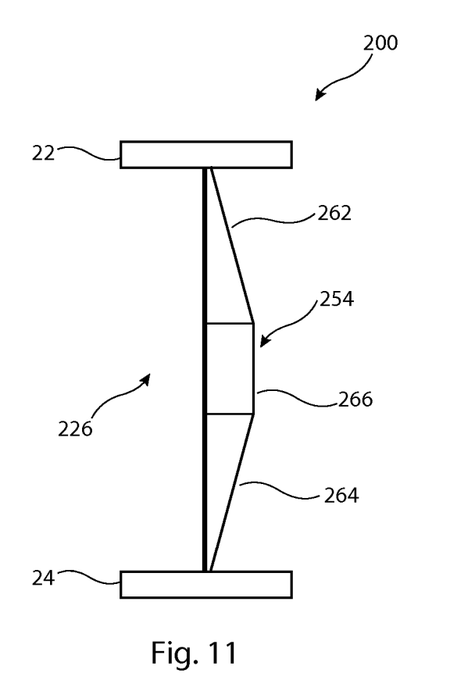
FIGS. 11 and 12 are side and front elevational views of the flow adjuster of FIG. 9.
Figure 12:
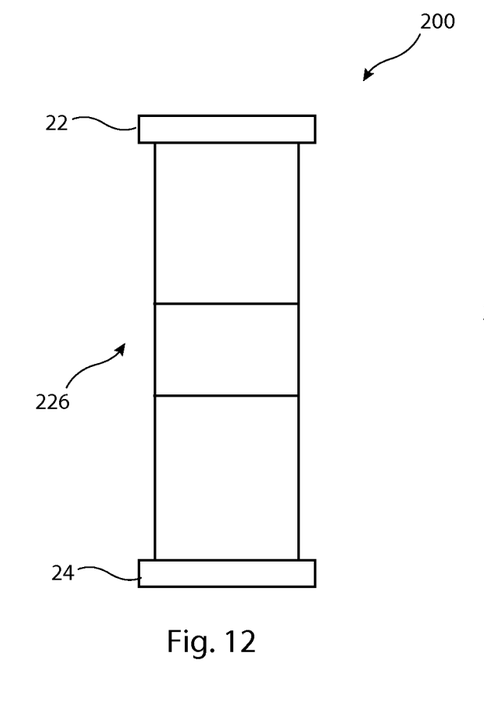
Figure 13:
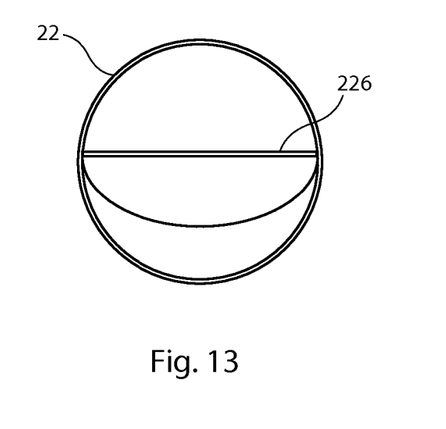
FIG. 13 is a plan view of the flow adjuster of FIGS. 10 to 12.

Another embodiment of flow adjuster 100 is shown in FIGS. 6 to 9, which show the device 100 in orientations equivalent to FIGS. 2 to 5, namely with FIG. 6 being a perspective view, FIG. 7 being a side elevational view, FIG. 8 being a front elevational view and FIG. 9 being a plan elevational view.

The flow adjuster 100 of this embodiment has a structure generally the same as that of the embodiment of FIGS. 2 to 5, namely with proximal distal supports 22, 24 equivalent to the supports of the first-described embodiment. The flow adjuster 100 includes an adjuster element 126 which is also a panel of impermeable or substantially impermeable material. In this embodiment, the panel 126 is substantially rectangular and substantially planar. As can be seen, it is disposed at an angle to longitudinal axis 150 of the device, as shown in particular in FIGS. 6 and 7. This is achieved by coupling the proximal end 132 of the panel 126 off-centre on the proximal support ring 22 and the distal end 136 of the panel 126 to an equivalent position at the other side of the distal ring 24. It will be appreciated that in this embodiment the proximal end distal ends 132, 136 of the panel 126 will not extend across the whole diameter of the support rings 22, 24. However, the major portion of the side edges of the panel 126 could be, as desired, wider relative to the proximal and distal ends 132, 136, such that the panel 126 has a transverse width which is the same as or similar to the diameter of the support rings 22, 24.

The panel 126 can have similar characteristics to the panel 26 of the embodiment of FIGS. 2 to 5.

The disposition of the panel 126 within the device 100 divides the lumen passing through the device into first and second sections or parts 140, 142, respectively. The first part 140, in this example, has a greater transverse cross sectional area at the proximal end 22 of the device 100, which gradually reduces to the distal end 24 of the device 100. By contrast, the part or section 142 has a smaller cross sectional area at the proximal end 22 of the device 100 and a greater cross sectional area at the distal end of the device. As with the embodiment of FIGS. 2 to 5, the first part or section 140 provides a narrowing passage through the device 100, whereas the section 142 provides a widening passage through the device. As a result, once the device is implanted within the vessel of a patient with the support rings 22, 24 held against the vessel walls, the first part 140 will provide a gradually reducing lumen through the device 100, with the result that blood flow through the section 140 will increase in pressure and flow speed from the proximal end to the distal end of the device 100, whereas fluid passing into the section 142 will reduce in pressure and speed from the proximal end 22 to the distal end 24 of the device. As a consequence, beyond the distal end 24 of the device, there will be a pressure differential across the vessel.

The embodiment of FIGS. 6 to 9 may have the features and characteristics of the embodiment of FIGS. 2 to 5 and the other embodiments disclosed therein.

With reference now to FIGS. 10 to 13, these show another embodiment of flow adjuster 200 which has a general configuration similar to that of the embodiments of FIGS. 2 to 5 and 6 to 9, that is with proximal and distal supports 22, 24, supporting a diverter element 226 in the form of a panel attached to and held by the proximal and distal supports 22, 24. In this embodiment, the panel 226 could be described as having a concave or recessed shape as one side 252 of the panel 226 is pressed inwardly while the opposing side 254 extends out of the plane in which the perimeter edges 232-238 of the panel 226 lie. In the particular example shown in FIGS. 10 to 13, the panel may have two tapering walls 262, 264 extending away from the peripheral plane to a centre point 266 which is substantially parallel to the peripheral plane. The specific shape of the panel 226 can vary from the embodiments shown in FIGS. 10 to 13.

As with the other embodiments, the panel 226 splits the lumen through the device 200 into first and second sections 240, 242 respectively. In this particular example, the proximal and distal edges 232, 234 of the panel 226 lie along the centreline of the support rings 22, 24 and therefore the proximal and distal ends of the sections 240, 242 have equal cross sectional areas. However, due to the shape of the panel 226, the section 240 will initially narrow and then widen again through the length of the device 200, whereas the section 242 will widen and then narrow through the length of the device. This will cause changes in fluid flow and pressure through the device 200, which assist in generating directional flow of fluid beyond the distal end of the device 200 as in practice passed the neck 14 of an aneurysm 12, as will be apparent from the following description.

Again, the embodiment of FIGS. 10 to 13 can have similar characteristics and features to the other embodiments described herein.

Figure 14:
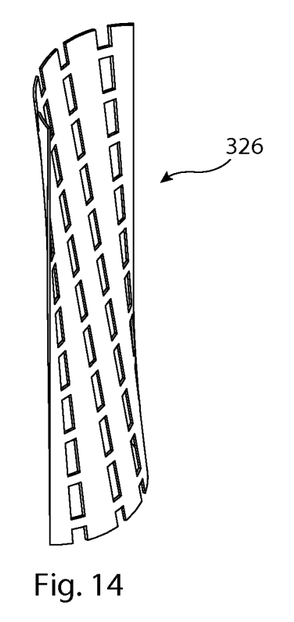
FIG. 14 shows in perspective another embodiment of flow diverter panel.

Referring now to FIG. 14, this shows another embodiment of flow adjuster element or panel 326 which in this embodiment comprises an array of perforations or holes 330 across its surface. The perforations 330 are substantially rectangular in shape and in this embodiment arranged in spaced columns and rows along the length of the panel 326. The perforations 330 are sufficiently small as to divert the majority of blood across the surface of the panel and have the primary function of increasing the flexibility and hence the compressibility of the panel 326, useful in allowing for the flow adjuster to be compressed to a narrow radius for deployment purposes. The perforations can for instance make it easier for the panel to twist on itself or otherwise collapse so as to compress the device radially for delivery purposes.

The perforations 330 may in some embodiments be in the form of slits, which in some embodiments may provide no gap in the surface of the panel 326 and therefore no apertures through which blood fluid may pass. This embodiment may perform in a similar manner to the embodiment shown in FIG. 14.

As will be apparent from FIG. 14, the panel 326 has a shape equivalent to the panel 26 of the embodiment of FIGS. 2 to 5. The panel 326 may have the same characteristics and be made of the same materials as the other panels disclosed herein. Similarly, the panel 326 may be used with supports 22, 24 as disclosed above.

Figure 15:
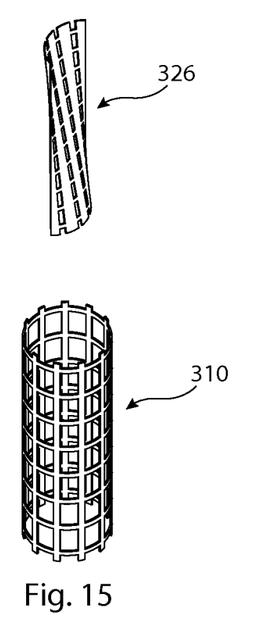
FIG. 15 is an exploded view of a flow diverter assembly using the panel of FIG. 14 and a support structure in the form of a stent.
Figure 16:
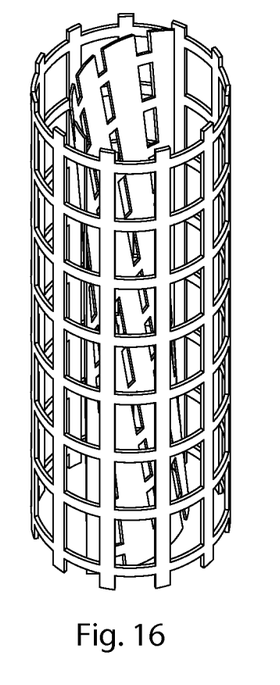
FIG. 16 shows the components of FIG. 15 assembled together in a completed flow diverter according to another embodiment of the present invention.

FIGS. 15 and 16 show another embodiment of flow adjuster assembly 300, with this being shown in exploded form in FIG. 15. In place of the separate support rings 22, 24 of the types disclosed above, there is provided a unitary support structure 310 which could be described as a stent. The structure 310 is in this example formed of a plurality of annular rings 332 which are coupled together by longitudinal struts 334 which extend the length of the support structure 310. The annular rings 332 and longitudinal struts 334 provide the proximal and distal supports for holding and supporting the proximal and distal ends of the panel 326 and may in some embodiments be coupled to the entire length of the edges of the panel 326. The stent structure 310 provides full support to the panel 326 rather than just at its ends. The rectangular arrangement of the rings 332 and struts 334 enables the stent 310 to be radially compressed for delivery purposes.

In other embodiments the support structure 310 can be very similar to that of a conventional stent, that is with sinusoidal or zigzag stent rings coupled by longitudinally extending tie bars.

It will be apparent that in all the embodiments taught herein the supports may be in the form of such a stent structure.

In other embodiments, the proximal and distal support elements could be coupled to one another, for example by appropriate struts or tethers.

It will be appreciated that with the embodiments described above and shown in the Figures, the device will operate the same way whichever way round it is placed in the vessel, subject to its angular orientation in the vessel, as described below.

Figure 17:
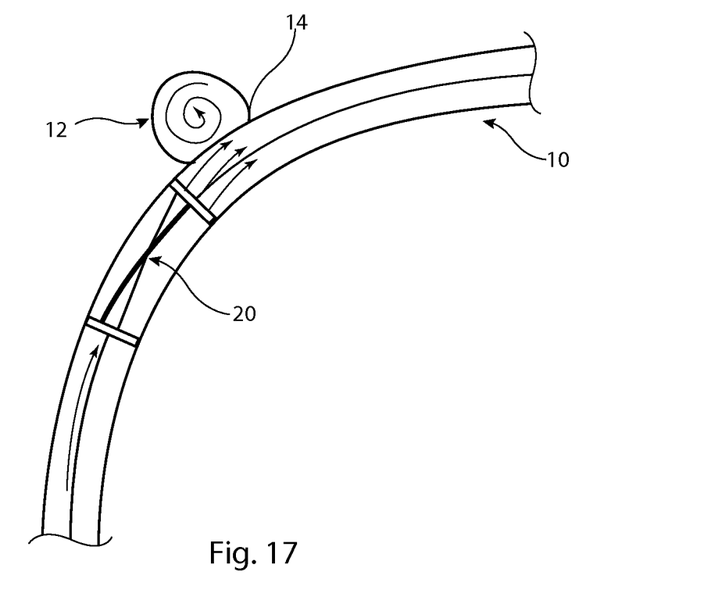
FIG. 17 is a schematic diagram in side elevation of the vessel of FIG. 1 with the flow adjuster of FIGS. 2 to 5 deployed therein.
Figure 18:
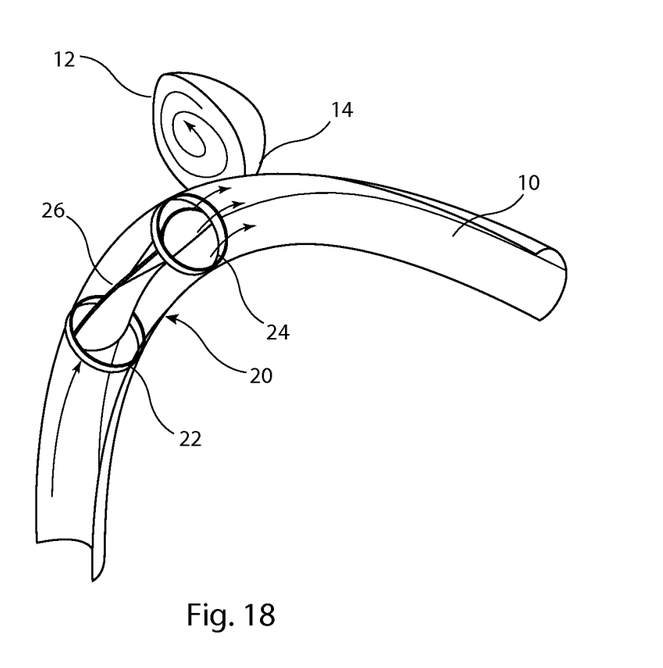
FIG. 18 is a schematic diagram in perspective of the vessel of FIG. 1 with the flow adjuster of FIGS. 2 to 5 deployed therein.

Referring now to FIGS. 17 and 18, these show the device of FIGS. 2 to 5 disposed within the vessel 10 of FIG. 1, just upstream of the aneurysm 12. In this example, the flow adjuster 20 is disposed such that the section of blood at higher pressure is adjacent the neck 14 of the aneurysm 12 while the section of blood of lower pressure is disposed on the opposite side of the vessel 10 to the aneurysm 12. In other words, the section 40 at the distal end 24 is adjacent the aneurysm neck 14.

The flow adjuster creates a pressure change within the flow of fluid at the distal end of the adjuster and in practice at the neck 14 of the aneurysm 12, which acts to divert blood away from the neck 14 of the aneurysm. This has the effect of reducing substantially the amount of blood which enters into the aneurysm. As a result, the substantially reduced flow of blood into the aneurysm 12, allows blood in the aneurysm sac to slow or stagnate, which reduces the wall sheer stress and over time will permit the smooth muscle cells within the tunica media to reform, contributing to the reformation of a healthy vessel without requiring direct treatment of the aneurysm itself.

It will be appreciated that the device has a generally cylindrical shape and can be made available in a range of lengths and diameters to suit a particular patient's anatomy and the vessel to which the device is to be deployed.

Not shown on the drawings are radiopaque markers on the device, which can be used to assist in the correct orientation and placement of the device within the patient. Such radiopaque markers are well known in the art and therefore are not described in detail herein or shown in the drawings.

The panel need not be made of a spring material or shape memory material and in some embodiments could be made of a relatively soft material, even a bioabsorbable material, possibly supported in its configuration by the proximal and distal support elements.

It is to be appreciated that the embodiments of flow adjuster taught herein may be provided with other features commonly found in implantable medical devices, for example anchoring elements in the form of barbs or the like, and retrieval elements such as hooks and the like for withdrawing device from a patient's vessel after completion of a medical procedure. It is envisaged also that the device could be retained permanently within a patient's vessel, not just to treat a formed aneurysm but also in order to prevent the formation of aneurysms or further aneurysms over time.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. A method of altering the characteristics of blood flow within the vessel of a patient including the steps of:
   deploying in a vessel an endoluminal flow adjuster having a diameter, a length delimited by proximal and distal ends, and providing a passage for the flow of fluid therethrough; the flow adjuster including at least one support structure providing proximal and distal supports spaced in a longitudinal direction of the flow adjuster between the proximal and distal ends; and an adjuster element including a panel having a length extending in the longitudinal direction, said panel being disposed between and supported by the proximal and distal supports, the panel dividing the passage through the flow adjuster into first and second parts varying in size over at least a part of the length of the flow adjuster;
   wherein the adjuster element causes blood flow in the vessel to be split into first and second parts having different flow velocities, the flow adjuster being deployed in an orientation in the vessel to create a pressure differential across the vessel at a treatment point of the vessel.

2. A method according to claim 1, including the step of orienting the flow adjuster to create a pressure differential across the width of the vessel at the entrance to the sac.

3. An endoluminal flow adjuster having a diameter, a length delimited by proximal and distal ends, and providing a passage longitudinally through the flow adjuster from the proximal end to the distal end where the proximal and distal ends are open for the flow of fluid through the passage; the flow adjuster including at least one support structure providing proximal and distal supports spaced in a longitudinal direction of the flow adjuster between the proximal and distal ends; and an adjuster element including a panel having a length extending in the longitudinal direction, said panel being disposed between and supported by the proximal and distal supports, the panel dividing the passage through the flow adjuster into first and second parts varying in size over at least a part of the length of the flow adjuster, wherein the passage defines an overall cross-sectional size perpendicular to the longitudinal direction, and the cross-sectional size of the first and second parts of the passage combine to define the overall cross-sectional size of the passage, and a ratio between the cross-sectional size of the first part and the cross-sectional size of the second part varies over at least a part of the length of the flow adjuster, wherein the first part of the passage is open at both the proximal and distal ends and the second part of the passage is open at both the proximal and distal ends such that fluid flow is maintained through both the first part and the second part.

4. An endoluminal flow adjuster according to claim 3, wherein the first and second parts provide unequal flow cross-sectional areas through the flow adjuster, thereby to create a fluid pressure differential between the first and second parts.

5. An endoluminal flow adjuster according to claim 3, wherein the first and second parts create two flows of fluid through the flow adjuster, one having a higher fluid pressure relative to the other.

6. An endoluminal flow adjuster according to claim 3, wherein the first and second parts are of unequal size along at least a portion of the flow adjuster.

7. An endoluminal flow adjuster according to claim 3, wherein the panel is formed of a sheet of material.

8. An endoluminal flow adjuster according to claim 3, wherein the panel is impermeable.

9. An endoluminal flow adjuster according to claim 3, wherein the panel has perforations or slots therein, the panel providing a barrier to blood therethrough.

10. An endoluminal flow adjuster according to claim 3, wherein the panel is of substantially uniform thickness.

11. An endoluminal flow adjuster according to claim 3, wherein the panel provides a flow constriction through the flow diverter in one of said first and second parts.

12. An endoluminal flow adjuster according to claim 11, wherein the flow constriction varies in transverse cross-sectional area along the length of the panel.

13. An endoluminal flow adjuster according to claim 3, wherein the panel is transversally curved to provide said first and second flow parts of unequal size.

14. An endoluminal flow adjuster according to claim 13, wherein the transverse curvature of the panel varies along the length of the panel.

15. An endoluminal flow adjuster according to claim 3, wherein the panel extends from a position close to one side of the flow adjuster at the proximal support to a position close to an opposing side of the flow adjuster at the distal support.

16. An endoluminal flow adjuster according to claim 3, wherein the panel has a concave or convex shape between the ends thereof.

17. An endoluminal flow adjuster according to claim 16, wherein the ends of the panel are substantially straight.

18. An endoluminal flow adjuster according to claim 3, wherein the proximal and distal supports are stents.

19. An endoluminal flow adjuster according to claim 3, wherein the proximal and distal supports are separate from one another.

20. An endoluminal flow adjuster having a diameter, a length delimited by proximal and distal ends, and providing a passage for the flow of fluid therethrough; the flow adjuster including at least one support structure providing proximal and distal supports spaced in a longitudinal direction of the flow adjuster between the proximal and distal ends; and an adjuster element including a panel having a length extending in the longitudinal direction, said panel being disposed between and supported by the proximal and distal supports, the panel dividing the passage through the flow adjuster into first and second parts varying in size over at least a part of the length of the flow adjuster,
    wherein the panel is attached to opposite sides of the proximal support and attached to opposite sides of the distal support, and the panel defines the first and second parts at both the proximal support and the distal support.

\* \* \* \* \*